United States Patent [19]

Houben et al.

[11] Patent Number: 5,567,478
[45] Date of Patent: Oct. 22, 1996

[54] PROCESS FOR PRODUCING A WATER-ABSORBING SHEET MATERIAL AND THE USE THEREOF

[75] Inventors: Jochen Houben, Kempen; Edgar Herrmann, Nettetal; Kurt Dahmen, Mönchengladbach, all of Germany

[73] Assignee: Chemische Fabrik Stockhausen GmbH, Krefeld, Germany

[21] Appl. No.: 454,818

[22] Filed: May 31, 1995

[30] Foreign Application Priority Data

Jun. 9, 1994 [DE] Germany .................. 44 20 088.9

[51] Int. Cl.⁶ ............................................ B05D 1/02
[52] U.S. Cl. .................. 427/342; 427/369; 427/389.9; 427/394; 427/421
[58] Field of Search ........................ 427/389.9, 394, 427/342, 369, 421

[56] References Cited

U.S. PATENT DOCUMENTS

| | | | |
|---|---|---|---|
| 4,340,057 | 7/1982 | Bloch et al. | 128/284 |
| 4,552,938 | 11/1985 | Mikita et al. | 526/240 |
| 4,659,793 | 4/1987 | Yang | 526/91 |
| 4,954,562 | 9/1990 | Anderson | 524/779 |
| 4,985,518 | 1/1991 | Alexander et al. | 526/240 |

FOREIGN PATENT DOCUMENTS

| | | |
|---|---|---|
| 1103644 | 4/1989 | Japan . |
| 4218502 | 8/1992 | Japan . |

OTHER PUBLICATIONS

Astract of JP 04–218502, Aug. 1992.
Abstract of JP 01–103644, Apr. 1989.

*Primary Examiner*—Shrive Beck
*Assistant Examiner*—Erma Cameron
*Attorney, Agent, or Firm*—Oblon, Spivak, McClelland, Maier & Neustadt, P.C.

[57] ABSTRACT

The present invention relates to a process for producing water-absorbing sheet-like materials which consist of a water-absorbent polymer and a prefabricated nonwoven fabric, wherein the prefabricated nonwoven fabric is impregnated with a solution comprising partially neutralized acrylic acid and at least one cross-linking agent and is squeezed to a certain coating amount, and the monomer solution thus applied is characterized in that the polymerization is carried out in the presence of radical initiators which cannot be activated thermally and at least one thermally activatable radical former used in addition. The additional use of a thermally activatable radical former in the polymerization results in products having a low residual monomer content, an improved water absorption under load, and a higher retention, with a production method being employed which is technically simple and economically efficient at the same time. The thermally activatable initiator portion may either be added to the monomer solution or applied to the substrate in an amount of 0.01 to 0.5 mole percent, relative to the monomer to be polymerized.

8 Claims, No Drawings

PROCESS FOR PRODUCING A WATER-ABSORBING SHEET MATERIAL AND THE USE THEREOF

The present invention relates to a process for the production of water-absorbing sheet-like materials consisting of a water-absorbent polymer and a prefabricated nonwoven (nonwoven fabric). The prefabricated nonwoven is impregnated with a solution of partially neutralized acrylic acid and squeezed off to a certain coating amount, and the monomer solution thus applied to the substrate is then polymerized, with the formed polymer and the prefabricated nonwoven combining intimately.

All of the previously described processes for the production of said in-situ polymers have the disadvantage that a large portion of the monomers is present in an unreacted form after termination of the actual polymerization. Since these monomers are critical from the toxicological point of view, they are reacted in a subsequent step or are removed otherwise. In general however, it is linear polymer chains of mean molecular weight that form, not the desired cross-linked polyacrylates. These polymer chains are soluble and cannot contribute to the water absorption, in particular under load, or to the water retention under load. In addition, from the application technological view, these portions have the undesired property of causing a slimy feel of the in-situ polymer after water absorption. Also, using one or more purely thermally activatable initiator entities, as proposed in EP 257 308, which are applied together with the monomer solution does not result in the desired products. In this case a minimum starting temperature must be kept for reasons of safety, which is clearly above that of a radical formation not induced by thermal activation. This high initial temperature results in short polymer chains and thus in poor application technological properties.

EP 123 500, U.S. Pat. No. 4,443,492, and EP 054 841 describe a washing process to aftertreat a formed fabric polymerized by means of electromagnetic or corpuscular ionizing radiation. However, this results in a high wastewater load with low-molecular and uncross-linked polyacrylic acids. The faster water absorption achieved thereby cannot compensate for this.

EP 223 908 describes the continuous production of a water-absorbing sheet-like material. The polymerization reaction of the monomer applied to the nonwoven is initiated by a large excess of radical formers. This results in products having a very high portion of residual monomers and a poor absorption behavior under pressure. In addition, it is difficult to store a solution of acrylic acid and, for example, potassium peroxide (example 1 of EP 223 908) without reactions with the activated double bond occurring. For this reason the content of oxide catalyst component in the monomer solution rapidly decreases during intermediate storage.

According to EP 251 314 the in-situ polymers, the residual monomer content of which is in the percentage region after radical polymerization, are irradiated by electromagnetic and corpuscular radiation of up to 100 Mrad. This expensive and—owing to the safety measures—also costly technique results in an uncontrolled secondary cross-linkage and yellowing of the products. Although the water absorption rate increases, the water absorption capacity does not at the same time.

In EP 257 308 the residual monomers are said to be reduced by additionally heating the still moist polymer to 100°–250° C. over an extended period (15 minutes). In this manner the acrylic acid is distilled off (boiling point 140° C., azeotropic mixture with water at 99.85° C., Advances in Chemistry, Series 116, Azeotropic Data III, p. 16). For this reason, this way of removing the residual monomers results in considerable problems with respect to air washing, and in addition is a waste of the starting materials. That is to say, the acrylic acid present in the exhaust air current cannot be recycled since the polymerization inhibitor, hydroquinone monomethyl ether, which is commonly used in the technical acrylic acid is also present in the exhaust gas.

EP 290 81 4 proposes the radiation with UV-light to reduce the amount of residual monomers. However, this requires increased capital expenditure and—owing to the lamps steaming up—increased maintenance expenses. In addition, it becomes apparent that this method of eliminating residual monomers is successful only if the polymer to be aftertreated has a water content of at least 20%-wt., and, in addition to water, comprises still unreacted peroxides. Since the water content in the exothermic polymerization considerably decreases owing to the large surface of the in-situ polymers, water has to be applied to the nonwoven. This is unfavorable from the energetic and economic point of view, since this water has to be evaporated again after radiation.

It is the object of the present invention to improve the hitherto known water-absorbing sheet-like materials which are manufactured of a nonwoven fabric and a polymer made on said nonwoven fabric in situ with respect to water absorption under load, retention, and content of residual monomers and soluble portions and, at the same time, to make the production process technically simple and economically efficient.

According to the present invention this object is achieved by the fact that for polymerization purposes first at least one thermally activatable radical former, preferably based on an azo compound, is used in addition to the radical initiators that cannot be activated thermally and which preferably are redox systems.

Accordingly, the subject matter of the present invention is a process for the production of water-absorbing sheet materials which consist of a water-absorbent polymer and a prefabricated nonwoven fabric, wherein the prefabricated nonwoven fabric is impregnated with a solution comprising partially neutralized acrylic acid and at least one crosslinking agent and is squeezed off to a certain coating quantity, and the monomer solution thus applied to the nonwoven fabric substrate is subsequently polymerized. Said process is characterized by the fact that the polymerization is carried out in the presence of radical initiators which cannot be activated thermally and, in addition, radical formers which are to be activated thermally.

It is preferred that a redox system be used as thermally inactivatable radical initiator entity.

Examples of thermally activatable radical initiators which—according to the present invention—are used in addition to the thermally inactivatable radical initiators include peroxides which, relative to the reducing component of the redox system, are used in excess: organic peroxides, in particular organic diperoxides, and particularly preferred, azo compounds, all of them having a suitable half-life.

The thermally activatable radical initiator entity used additionally according to the present invention may either be sprayed on the monomer-coated nonwoven fabric or better—because of homogenous distribution—directly applied on the nonwoven substrate in the form of a dissolved compound with the monomer solution. The thus applied thermally activatable radical former is activated by the reaction heat of the exothermic polymerization and supplies the radicals necessary to continue polymerization.

In order to be sufficiently effective, the compounds used as thermally activatable radical formers must be chosen such that they do not decompose in the prepared monomer solution but do so in the course of the polymerization or after thermal activation, however, at 110° C. at the latest with a half-life of less than 60 minutes.

The appropriate choice of the thermally activatable radical initiator makes it possible to adjust the time at which the polymerization initiated by this compound starts. The application technological properties may be influenced in this way. The amount of thermally activatable initiator which is homogeneously distributed in the polymer can minimize the amount of remaining residual monomers. Also, it is possible to use a mixture of several thermally activatable initiator entities in different concentrations. For economic reasons the added amount of thermally activatable initiators should be such that it is just effective in eliminating the monomers.

Azo compounds, such as 2,2'-azobis[2-(2-imidazoline-2-yl)propane]dihydrochloride, azobis (2-amidinopropane)dihydrochloride (A.B.A.H.), or azo-bis-cyanopentanoic acid (distributor: Wako) may be used as preferred thermally activatable initiators. The decomposition temperatures of these exemplary azo compounds are known. Although previous experience has shown that the half-value temperature is higher by some degrees in an acrylate solution, this value may serve as a guide.

Suitable substrates include any open-structured, flat-shaped fibrous structure, such as nonwovens and wovens, which, owing to its elasticity, has a deformation value after a pressure load. Hydrophilic nonwovens are preferred; for example, the polyester staple-fiber-nonwovens distributed under the tradename Sawafill by the firm of Sandler. These nonwovens are produced and distributed in the form of rolls having a width of 1.50 m or more. The term "nonwovens" is to be understood as those materials included in the definition established by EDANA (European Disposables and Nonwovens Association). Since oxygen has an enormous inhibitory capacity on polymerization reactions and the monomer solution applied on the nonwoven has a very large surface, the oxygen content prior to and during polymerization must be reduced within the whole apparatus by means of suitable technical measures. Oxygen contents in the atmosphere of below 100 ppm are desirable. Such low oxygen traces can be measured by means of devices manufactured by the firm of Systech (types EC 91 or EC 90M) or Orbisphere (system MOCA), for example.

Acrylic acid in partially neutralized form as sodium, potassium, or ammonium salt or as their mixture is primarily suitable as monomer for the water-absorbing polymer. It is possible to admix other monomers. In general, the content of monomers amounts to 2–8 mol/l. In addition, a cross-linking agent in the amount of 0.02–1.0 mol-%, relative to the monomer content; the thermally activatable initiator or initiator combination in an amount of 0.01–0.5 mol-%, relative to the monomer content; as well as the reducing component of the oxidation-reduction pair (e.g., ascorbic acid) which initiates the reaction in an amount of 0.005–0.1 mol-%, relative to the monomers, are added to the monomer solution. Examples of suitable crosslinkers include compounds having two or more monoolefinic groups capable of being incorporated by polymerization or having groups capable of reacting with carboxyl groups; or compounds having at least one group reactive with carboxyl groups and at least one polymerizable, monoolefinic group, e.g., methylenebisacrylamide, triallylamine, trimethylolpropane triacrylate, ethylene glycol bisglycidyl ether, or the bismethacrylic acid ester of triethylene glycol. The monomer solution is prepared at a temperature of 5°–40° C. in the padding bath. A small amount of oxygen (1–10 ppm) should be left in the monomer solution to prevent premature polymerization initiated by the decomposition of the preferred azo initiator. This is necessary because the usually added stabilizer, hydroquinone monomethyl ether, acts in the presence of oxygen only.

The dry nonwoven fabric is first passed through two squeeze rolls in order to expel contained air and then drawn through a trough filled with monomer solution. Subsequently, the impregnated nonwoven is led through two squeeze rolls again, causing continuous distribution of the monomer solution on the nonwoven and, at the same time, a constant liquor amount adjustable through the contact pressure. Devices for the impregnation are known from continuous dyeing (padding) and are commonly called foulards or padding machines. A description thereof can be found, for example, in Ullmann, Encyklopädie der technischen Chemie, 4. Auflage vol. 22, page 711. In addition to the contact pressure, the applied amount of liquor can also be adjusted through the viscosity of the monomer solution, the conveying rate, the hydrophilicity, and the thickness of the substrate. The principle use of such a technique of applying monomer solutions to prefabricated substrates is described in EP 54 841.

After application of the monomer solution, the impregnated fabric is carried on and the polymerization started by spraying an aqueous solution of 0.005–1.0 mol-% (relative to monomer) of the oxidizing component. Water-soluble or water-dispersible inorganic oxides, such as hydrogen peroxide or potassium persulfate, or organic compounds, for example, t-butyl hydroperoxide, are suitable oxidizing components. This catalyst component should be distributed over the impregnated fabric in the finest possible manner, avoiding escape of undesired fogs from the apparatus. The fineness of distribution may be adjusted by the type of nozzles, the number of nozzles, the amount of added nitrogen current, and by the dilution with water. It may be advantageous to apply the solution of the oxidizing component in a precooled form (0°–20° C.).

The exothermal polymerization started by the preferred redox reaction must be carried out with a sufficient conversion in order to decompose the azo initiators already added with the monomer solution. This causes a continued radical formation connected with a further polymerization which includes the remaining monomers. The maximum polymerization temperature can be adjusted by the effective concentration of the monomer solution, the starting temperature, the kind and concentration of the redox initiators. The further polymerization process can also be supported by means of heat supply; parallel to the final polymerization the drying degree of the final product may be improved by this. Superheated steam, hot nitrogen, or radiation heat, e.g., generated by IR dark body radiators, are suitable forms of supplying heat.

However, since the polymerization may also be conducted such that a dry polymeric nonwoven, for example, is obtained as end product, this can be stored in the obtained form, transported, and further processed. Optionally, the initially obtained material according to the present invention is subjected to the polymerization procedure again. The material according to the present invention may also be subjected to a surface-cross-linking aftertreatment, e.g., using polyols, alkylene glycol glycidyl ethers and/or alkylene carbonates. Further processing may include the process steps of breaking, cutting, rolling, punching, and winding up, for example. The finished material according to the present invention normally comprises less than 20%, preferably less then 10% of water. As compared to the previously described in-situ polymers, the products according to the present invention stand out for an improved water absorption under load, an improved water retention under load, and lower contents of residual monomers and soluble components.

The in-situ polymer thus formed is primarily used in hygienics, in particular in disposable diapers and sanitary napkins, and in sanitary engineering. It is also possible to use them in planting mats, or during the storage of liquid-releasing food in flat pans. After polymerization and drying the web-type material may either be reeled up into rolls having the width of production or cut in advance to the later processing width.

Test Methods

Absorption:

To determine the absorption, 5 cm$^2$ of the in-situ polymer is enclosed in a tea bag and dipped in 0.9% solution of sodium chloride for 20 minutes. The tea bag is removed from the solution, dropped off for 10 minutes, and weighed. One tea bag without in-situ polymer is used as blank.

$$\text{Absorption} = \frac{\text{Weight} - \text{Blank reading} - \text{Initial weight}}{5 \text{ cm}^2}$$

Absorption under load:

The absorption under load (pressure load 20 g/cm$^2$=0.3 psi and 60 g/cm$^2$=0.9 psi) is determined according to a modification of the method described in EP 339 461, page 7: In a cylinder provided with sieve bottom (diameter 6 cm) a circular, appropriately cut piece of the in-situ polymer is placed and loaded with a punch exerting a pressure of 20 g/cm$^2$ (60 g/cm$^2$). The cylinder is then placed in a dish containing 0.9% sodium chloride solution, and the superabsorber is allowed to suck 0.9% sodium chloride solution for 1 hour.

$$\text{Absorption under load} = \frac{\text{Weight} - \text{Initial weight}}{28.26 \text{ cm}^2}$$

Retention;

Determination of the retention is carried out in the same manner as used for the absorption, except that after hanging the tea bag is centrifuged for 5 minutes in a centrifuge (diameter 23 cm, 1,400 rpm).

$$\text{Retention} = \frac{\text{Weight} - \text{Blank reading} - \text{Initial weight}}{5 \text{ cm}^2}$$

Soluble portions:

About 1.0 g of the in-situ polymer is stirred with 185 ml of 0.9% NaCl-solution in a 250-ml-Erlenmeyer flask with ground joint for one hour at 500 rpm by means of a 3 cm finger paddle. Subsequently, filtering off is carried out by means of a suction bottle. 20.00 g of the flitrate is set to pH 10.0 using sodium hydroxide solution and titrated with 0.1 n HCl to a pH of 2.70. The proportion of soluble components is calculated on the basis of HCl-consumption; it stands to reason that the comonomer units without carboxyl groups are not included and must be corrected, if necessary.

Residual monomers:

The residual monomers are also determined from the above flitrate by means of HPLC and evaluated according to the process of internal standard.

The present invention will be illustrated in more detail by the following examples:

EXAMPLE 1

0.9282 g (0.0068 mole) of triallylamine, 309.4 g (4.3 mole) of acrylic acid, 311 g of water, and 240.4 g (3.005 mole) of sodium hydroxide solution (50%) are brought together under cooling. The solutions of 1.0 g (0.0028 mole) azobis-(2-amidinopropane)dihydrochloride (A.B.A.H.) in 10 g of water and 0.45 g (0.0026 mole) ascorbic acid in 10 g of water are added to said monomer solution. This monomer solution having a neutralization degree of 70% and a monomer content of 4.85 mol/l is purged with nitrogen until the remaining oxygen content in the solution is in the range of 5–6 ppm (measurement with OMI 196, of Orbisphere), and it is placed in the foulard at 20° C. Subsequently, a polyester staple fiber nonwoven having a width of 30 cm (Sawafill 1122, of Sandler) is introduced into the apparatus which is under a slight nitrogen overpressure and drawn through the foulard. The impregnated nonwoven is squeezed off to the desired amount of coating between a pair of squeeze rollers, and the polymerization is started by spraying a 1% hydrogen peroxide solution. The maximum polymerization temperature is reached after about one minute, and the polymerization is completed by switching in flat IR-radiators (of Elstein, type HLF, 400 watt per radiator).

EXAMPLE 2

The same procedure as above, except that a combination of 0.71 g (0.002 mole) of azobis-(2-amidinopropane)dihydrochloride and 0.56 g (0.002 mole) of azocyanopentanoic acid was used instead of the above indicated amount of azobis-(2-amidinopropane)dihydrochloride.

EXAMPLE 3

Procedure as in Example 2, except that the azocyanopentanoic acid was substituted for 0.65 g of 2,2'-azobis[2-(2-imidazoline-2-yl)propane]dihydrochloride and that the initiators were added to the monomer solution not until a temperature of 5° C. was reached and that this was stored at said temperature. The reaction was initiated by spraying a 2% hydrogen peroxide solution. Following polymerization, the in-situ polymer was dried with a preheated nitrogen current.

EXAMPLE 4

135.7 g of acrylic acid (1.88 mole), 164.2 g of KOH (45%) (1.32 mole), 0.6 g of triallylamine, 0.3 g of trimethylolpropane triacrylate, and 0.5 g of ascorbic acid are brought together under cooling. A solution of 0.45 g A.B.A.H. in 2 g of water is added thereto. This solution having a monomer concentration of 6.2 mol/l and a neutralization degree of 70% was applied at 30° C. The reaction was initiated by spraying a 1% solution of t-butyl hydroperoxide and terminated without further energy supply.

EXAMPLE 5

Procedure as in Example 1, except that 2.4 g (0.01 mole) of diethylene glycol dimethacrylate (Bisomer DEGMA, manufacturer ISC) was used instead of the triallylamine.

EXAMPLE 6

The same procedure as in Example 2, but the amounts of the two azo compounds were triplicated.

COMPARATIVE EXAMPLES

EXAMPLE 7

The same procedure as in Example 1, except that the azo compound A.B.A.H. was omitted without substitution.

EXAMPLE 8

(Corresponds to Example 1 of EP 257 308)

250 g (3.125 mole) of 50% sodium hydroxide solution, 265 g of water, 300 g (4.17 mole) of acrylic acid, and 0.3 g (0.002 mole) of N,N'-methylenebisacrylamide were mixed under ice cooling. The aqueous solution had a neutralization degree of 75% and a monomer concentration of 5.1 mol/l. The solution was rendered inert using nitrogen and heated to 50° C. Then, 0.6 g (0.002 mole) of potassium persulfate was added. This solution was placed in the padding machine at 50° C., and a polyester staple nonwoven was impregnated with it. The polymerization was initiated by spraying a 5% solution of sodium hydrogensulfite in water, but it started not until 16 g of the hydrogensulfite solution had been applied. The moisture content was adjusted to 20%, and the in-situ polymer was heated for 15 minutes at 170° C. in the circulating air drier. A yellowish, rigid nonwoven was obtained.

EXAMPLE 9

(Corresponds to Example 2 of EP 223 908)

324 g (4.5 mole) of acrylic acid, 222 g (3.36 mole) of solid 85% KOH, 180 g of water, and 1.0 g (0.006 mole) of N,N'-methylene-bisacrylamide were brought together under cooling. At the end, 1.9 g of 35% (0.0175 mole) hydrogen peroxide was added. The above described polyester nonwoven was coated with this solution. The impregnated nonwoven was preheated to 100° C. by means of IR dark body radiators (of Elstein) and sprayed with a 7% solution of monoethanolamine, whereupon the polymerization started.

The properties of the obtained products were examined; the results are listed in Table 1.

(a) impregnating a prefabricated nonwoven fabric with a solution comprising partially neutralized acrylic acid or methacrylic acid, at least one cross-linking agent, at least one thermally activatable radical former, and the reducing component of an oxidation-reduction pair;

(c) squeezing the impregnated nonwoven fabric;

(d) initiating polymerization of the impregnated solution by applying a solution of the oxidizing component of the oxidation-reduction pair to the impregnated nonwoven fabric; and (e) allowing polymerization to proceed to completion.

2. The process according to claim 1 characterized in that at least one azo compound is used as thermally activatable radical former.

3. The process according to claim 1, characterized in that the thermally activatable radical former has a half-life of less than or equal to 60 minutes at 110° C.

4. The process according to claim 2 characterized in that 2,2'-azobis[2-(2-imidazoline-2-yl)propane]dihydrochloride, azobis (2-amidinopropane)dihydrochloride (A.B.A.H.), and/or azo-bis-cyanopentanoic acid are used as azo compounds.

5. The process according to claim 1 characterized in that the acrylic acid or methacrylic acid is partially neutralized as the salt of sodium, potassium, or ammonium, or as a mixture thereof.

6. The process according to claim 1 characterized in that the cross-linking agent of claim 1 has at least two functional monoolefinic groups or groups reactive with carboxyl groups.

7. The process according to claim 1 characterized in that the thermally activatable radical former is used in amounts ranging from 0.01 to 0.5 mol-%, relative to the amount of acrylic acid or methacrylic acid.

8. The process according to claim 1 characterized in that the thermally activatable radical former is used in amounts ranging from 0.01 to 0.1 mol-%, relative to the monomer amount.

* * * * *

TABLE 1

| | Test results of Examples 1–9: | | | | | | | | |
|---|---|---|---|---|---|---|---|---|---|
| Examples | 1 | 2 | 3 | 4 | 5 | 6 | 7 | 8 | 9 |
| Polymer concentration | 195 g/m² | 190 g/m² | 200 g/m² | 195 g/m² | 200 g/m² | 195 g/m² | 195 g/m² | 185 g/m² | 200 g/m² |
| Absorption | 4450 g/m² | 4560 g/m² | 4870 g/m² | 3860 g/m² | 7780 g/m² | 4830 g/m² | 6100 g/m² | 6200 g/m² | 5950 g/m² |
| Retention | 3705 g/m² | 3800 g/m² | 4050 g/m² | 3220 g/m² | 4980 g/m² | 3750 g/m² | 1320 g/m² | 1450 g/m² | 2840 g/m² |
| AUL 0.3 psi | 3100 g/m² | 3200 g/m² | 3200 g/m² | 3110 g/m² | 4740 g/m² | 3160 g/m² | 1040 g/m² | 1130 g/m² | 1250 g/m² |
| AUL 0.9 psi | 1250 g/m² | 1340 g/m² | 1320 g/m² | 1650 g/m² | 1130 g/m² | 1380 g/m² | <500 g/m² | <500 g/m² | <500 g/m² |
| Soluble portions | 3.10% | 4.00% | 4.10% | 3.90% | 3.70% | 1.80% | 18% | 9.50% | 5.50% |
| Residual monomers | 450 ppm | 280 ppm | 320 ppm | 420 ppm | 430 ppm | 180 ppm | 6500 ppm | 400 ppm | 5800 ppm |
| Moisture | 4.50% | 4.50% | 4.40% | 4.70% | 4.35% | 4.40% | 6.30% | 2.10% | 4.30% |

What is claimed is:

1. A process for the production of water-absorbing sheet materials, comprising the steps of: